United States Patent
Goedeke

(12) 
(10) Patent No.: US 6,463,329 B1
(45) Date of Patent: Oct. 8, 2002

(54) NULL-FREE ANTENNA ARRAY FOR USE IN COMMUNICATION WITH IMPLANTABLE MEDICAL DEVICES

(75) Inventor: Steven D. Goedeke, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 12 days.

(21) Appl. No.: 09/629,999

(22) Filed: Aug. 1, 2000

(51) Int. Cl.[7] .................................................. A61N 1/37
(52) U.S. Cl. ........................................................ 607/60
(58) Field of Search .............................. 607/60, 30, 31, 607/32; 128/899

(56) References Cited

U.S. PATENT DOCUMENTS

| | | | |
|---|---|---|---|
| 4,531,523 A | 7/1985 | Anderson | 128/419 |
| 4,542,532 A | 9/1985 | McQuilkin | 455/78 |
| 5,113,869 A | 5/1992 | Nappholz et al. | 128/696 |
| 5,311,449 A | 5/1994 | Adams | 364/514 |
| 5,324,315 A | 6/1994 | Grevious | 607/60 |
| 5,345,362 A | 9/1994 | Winkler | 361/681 |
| 5,404,877 A | 4/1995 | Nolan et al. | 128/671 |
| 5,527,348 A | 6/1996 | Winkler et al. | 607/30 |
| 5,562,714 A | 10/1996 | Grevious | 607/32 |
| 5,565,005 A | 10/1996 | Erickson et al. | 607/51 |
| 5,630,835 A * | 5/1997 | Brownlee | |
| 5,683,432 A | 11/1997 | Goedeke et al. | 607/32 |
| 5,697,958 A | 12/1997 | Paul et al. | 607/31 |
| 5,720,770 A | 2/1998 | Nappholz et al. | 607/30 |
| 5,766,232 A | 6/1998 | Grevious et al. | 607/60 |
| 5,861,019 A | 1/1999 | Sun et al. | 607/60 |
| 6,009,878 A | 1/2000 | Weijand et al. | 128/899 |
| 6,169,925 B1 * | 1/2001 | Villaseca et al. | |
| 6,298,271 B1 * | 10/2001 | Weijand | |

* cited by examiner

*Primary Examiner*—Scott M. Getzow
(74) *Attorney, Agent, or Firm*—Girma Wolde-Michael; Michael C. Soldner

(57) ABSTRACT

An improved telemetry head that employs two coils is disclosed. A first, larger diameter outer coil is generally employed to initiate telemetric communication between the programmer or monitor and the implanted device. In the event that successful communication is not accomplished using the outer coil, the programmer or monitor attempts communication using the inner coil. Any resultant reduced signal strength that may be associated with use of the smaller diameter inner coil is acceptable based on the assumption that the antenna of the implanted device is located in the null associated with the outer antenna coil and thus is located in close proximity to the inner coil. To prevent loss of signal strength, addition turns may be employed to implement the inner coil. In one embodiment, at least one of the first and second coils is of a dual-coil configuration having two coils in series opposition to improve the signal-to-noise ratio.

16 Claims, 10 Drawing Sheets

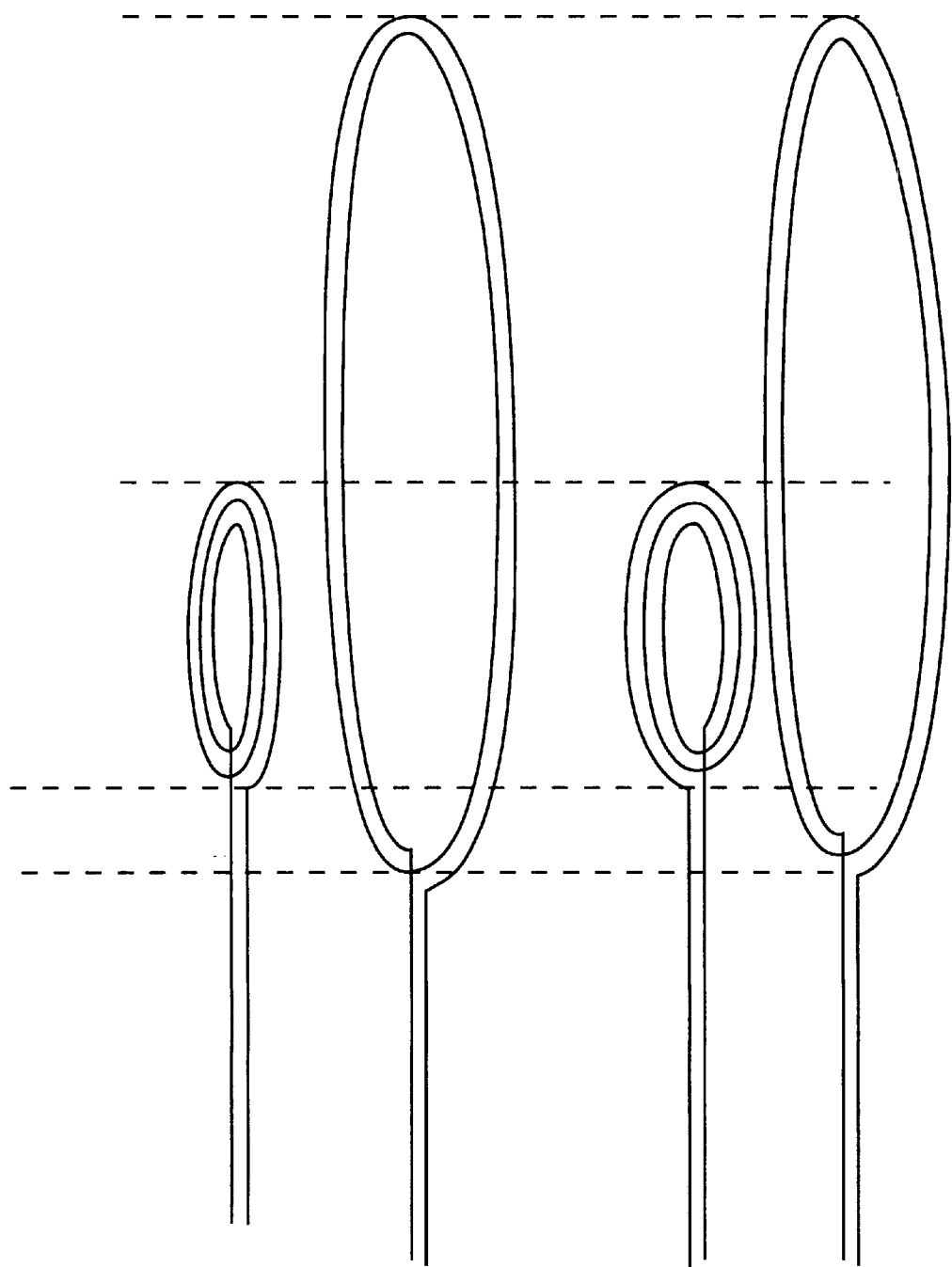

NULL-FREE ANTENNA ARRAY FOR USE IN COMMUNICATION WITH IMPLANTABLE MEDICAL DEVICES

BACKGROUND OF THE INVENTION

This invention relates generally to programmers or monitors intended for use with implantable medical devices and more specifically to antennas adapted for communication between implanted medical devices and external programmers or monitors.

In the context of implantable medical devices, it has become common to provide a communication link between the implanted device and an external programmer or monitor in order to allow for transmission of commands from the external device to the implanted device and to allow for transmission of stored information and/or sensed physiological parameters from the implanted device to the external programmer. Conventionally, communication between an implanted device and an external programmer or monitor has been accomplished by means of a telemetry system which includes a transceiver located within the implanted medical device and an external programmer or monitor, each having a radio transmitter/receiver and an associated antenna.

The implanted device typically includes an antenna located either within the hermetic device housing containing the circuitry, as disclosed in U.S. Pat. No. 4,542,532 issued to McQuilkin, in a plastic header or connector block used to interconnect the device to electrical leads as disclosed in U.S. Pat. No. 5,697,958 issued to Patrick et al. or mounted to the device housing as in U.S. Pat. No. 5,861,019 issued to Sun et al. and U.S. Pat. No. 5,720,770 issued to Nappholz et al., all incorporated herein in their entireties. The programmer or monitor typically includes or consists of a telemetry head containing an antenna, intended to be placed on the patient's body in close proximity to the implanted device. The telemetry head may be coupled to the external programmer or monitor by means of a cord, as disclosed in U.S. Pat. No. 5,766,232 issued to Grevious et al. In alternative systems, as described in U.S. Pat. No. 5,404,877 issued to Nolan and U.S. Pat. No. 5,113,869 issued to Nappholz, the programmer or monitor may be provided with an antenna located some feet away from the implanted device.

One common telemetry head antenna configuration is a coil antenna mounted parallel to a major surface of the telemetry head's outer enclosure, which surface is located on or closely adjacent the patient's body during telemetric communication. Such telemetry heads are disclosed in U.S. Pat. Nos. 5,527,348 and 5,562,714, both incorporated herein by reference in their entireties. Coil antenna telemetry systems such as these have the disadvantage that they display a signal strength minimum or "null" in the region directly beneath and close to the coil. In the context of telemetry systems employing transmission antennas located at substantial distances from their associated receiving antennas, one solution to eliminating null spots has been to provide diversity antenna arrays employing antennas which are either oriented to display different polarizations or are separated spatially from one another. Examples of such antenna arrays are disclosed in U.S. Pat. No. 6,009,878 issued to Wiejand. In the context of programmers for implantable medical devices, the problem of nulls is generally addressed by the physician moving the telemetry head relative to the implanted device until an appropriate spatial relationship is attained.

SUMMARY OF THE INVENTION

The present invention is directed toward an improved telemetry head which employs two coils that may alternatively be employed to communicate with the implanted device. A first, larger diameter outer coil is generally employed in conjunction with initiation of telemetric communication between the programmer or monitor and the implanted device. The telemetry head is first placed in a location that the physician believes to be located generally over the implanted device, and the larger diameter outer coil is first employed in an attempt to initiate telemetric communication with the implanted device. In the event that successful communication is not accomplished using the outer coil, programmer or monitor attempts communication using the inner coil, under the assumption that the implanted device is located directly under some portion of the outer coil at a relatively shallow depth, falling into the null. Any resultant reduced signal strength that may be associated with use of the smaller diameter inner coil is acceptable based on the assumption that the antenna of the implanted device is located in the null associated with the outer antenna coil and thus is located in close proximity to the inner coil. It may be noted that additional coil turns may be used to implement the smaller inner coil to maintain signal strength. Only if successful communication between the programmer and the implanted device cannot be accomplished using either of the two coils, will the physician be required to move the telemetry head to an alternative location. Therefore, in the particular circumstances associated with telemetry heads used in close proximity to implanted medical devices, the multi-coil antenna array provides a simple and elegant mechanism for simplifying the process of locating the telemetry head relative to the implanted device.

BRIEF DESCRIPTION OF THE DRAWINGS

FIG. 7 is a diagram illustrating an inner and outer coil antenna wherein the inner and outer coils are not concentric or co-planar.

FIG. 10 is a diagram illustrating an inner and outer coil antenna wherein one of the inner coils is co-planar with

DETAILED DESCRIPTION OF THE PREFERRED EMBODIMENTS

Figure 1:
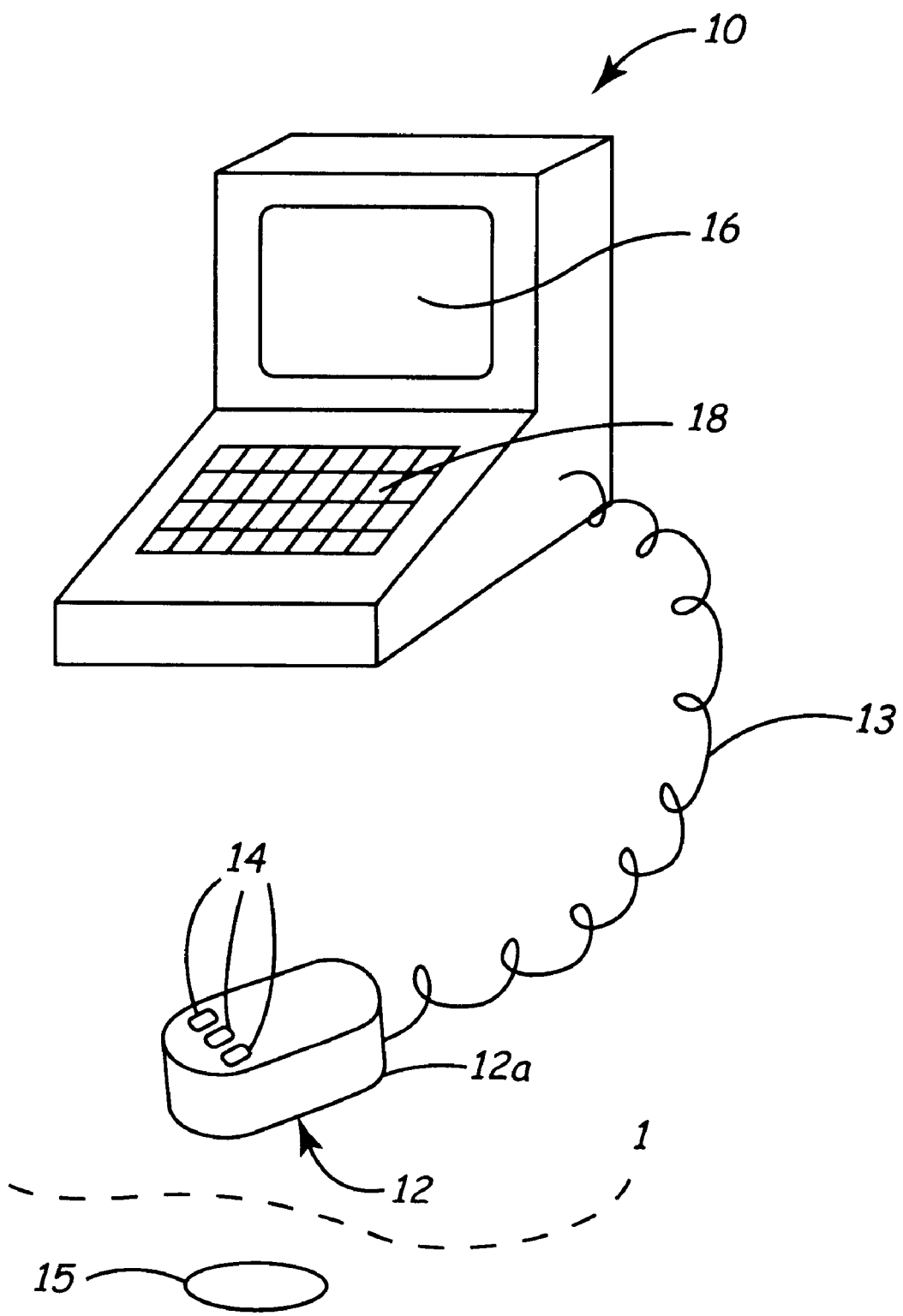
FIG. 1 is a perspective view of a programmer or monitor provided with a telemetry head according to the present invention.

FIG. 1 is an illustration of a programmer or monitor and associated telemetry head incorporating the present invention. The programmer or monitor 10 is provided with a display 16 which may be employed to display information received from or to be sent to an implanted device. Keyboard 18 is employed control the operation of the programmer or monitor, to select parameters for the implanted device, and to determine the sorts of information desired to be received from the implanted device. A touch sensitive display may of course be substituted for separate keyboards and display, for example as disclosed in U.S. Pat. No. 5,345,362, issued to Winkler, incorporated herein by reference in its entirety.

The telemetry head 12 is illustrated as coupled to the programmer or monitor 10 by means of a coiled multiconductor cable 13, and is provided with one or more indicators and/or switches 14 which may be employed as switches and indicators have typically been employed in the context of programmers for implantable devices, including as indicators of a valid telemetry link and as controls for initiating telemetry transmissions. For example, such indicators and control buttons are included in U.S. Pat. No. 5,324,315 issued to Grevious and incorporated herein by reference in its entirety. The lower major surface 12a of the telemetry head is intended to be placed on or adjacent the skin 17 of the patient. Located within telemetry head 12 are two concentric, generally co-planar coil antennas located parallel to the lower major surface 12a of the telemetry head, each coupled to the programmer or monitor 10 by means of cable 13. Programmer or monitor 10 is provided with an R-F transceiver located therein, which may be selectively coupled to either of the two coil antennas in the telemetry head 12 by means of an R-F switching circuit, located either internal to programmer or monitor 10 or internal to telemetry head 12. In additional alternative embodiments, the R-F transceiver circuitry may also be located internal to telemetry head 12, or the entire programmer or monitor may be incorporated into a unitary, hand held device, for example as disclosed in U.S. Pat. No. 5,311,449 issued to Adams, and U.S. Pat. No. 5,565,005 issued to Erickson.

Illustrated at 15 is an implanted pacemaker, located under the skin of the patient, indicated by broken line 17. In use, the telemetry head 12 is placed on the patient's skin 17, over the implanted pacemaker 15, and an attempt to establish a telemetry link is first made using the outermost of the two coils located within telemetry head 12. In response to a failure to establish a communication link using the outermost of the two coils, the innermost of the two coils is then employed in an attempt to establish a telemetry link with the implanted device 15, on the assumption that it is located in the null directly under a portion of the outermost coil. In the event that neither coil may be successfully employed to establish a telemetry link, the physician will move the telemetry head slightly, in an effort to find a better location, in a manner analogous to that employed by prior art single-coil or dual-coil telemetry heads.

Figure 2:
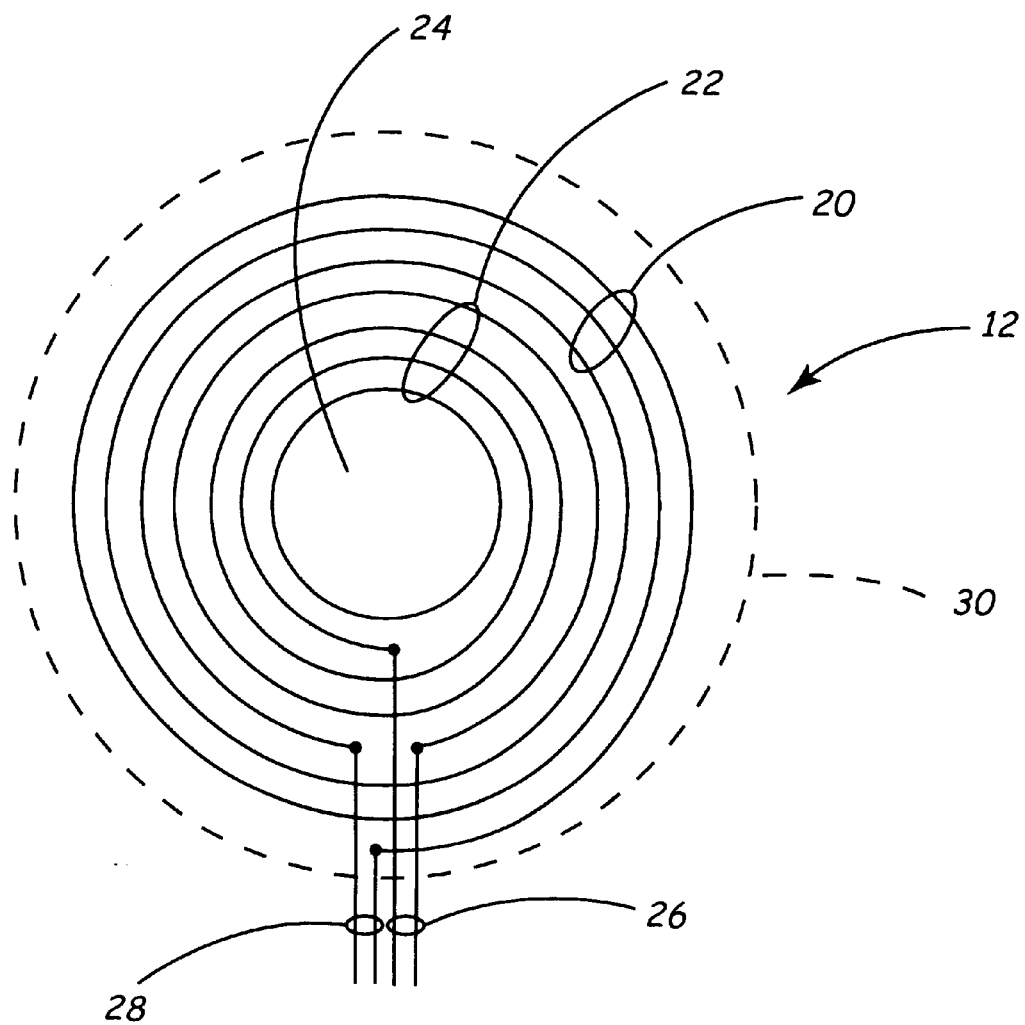
FIG. 2 is a schematic view of a telemetry head according to the present invention.

FIG. 2 is a schematic illustration of the structure of the telemetry head 12, with the enclosure 30 of the telemetry head 12 indicated by broken line. Located within the enclosure 30 are two multi-turn coil antennas 20 and 22, each coupled to a pair of mutually insulated conductors, 28 and 26. Conductor pairs 26 and 28 may extend to the programmer 10 (FIG. 1) within the cable 13, or alternatively, may be coupled to switching circuitry located within the telemetry head enclosure 30. Optionally located within the inner coil 22 is a permanent magnet 24 to be employed in activating the reed switch on those implanted devices in which reed switches are employed in conjunction with telemetry operations. The physical structure of the telemetry head 12 may, for example, correspond to that illustrated in U.S. Pat. No. 5,527,348 issued to Winkler et al. and incorporated herein by reference in its entirety, with the exception that two concentric coils are located in the telemetry head rather than a single coil as illustrated in the Winkler et al. patent.

Figure 3:
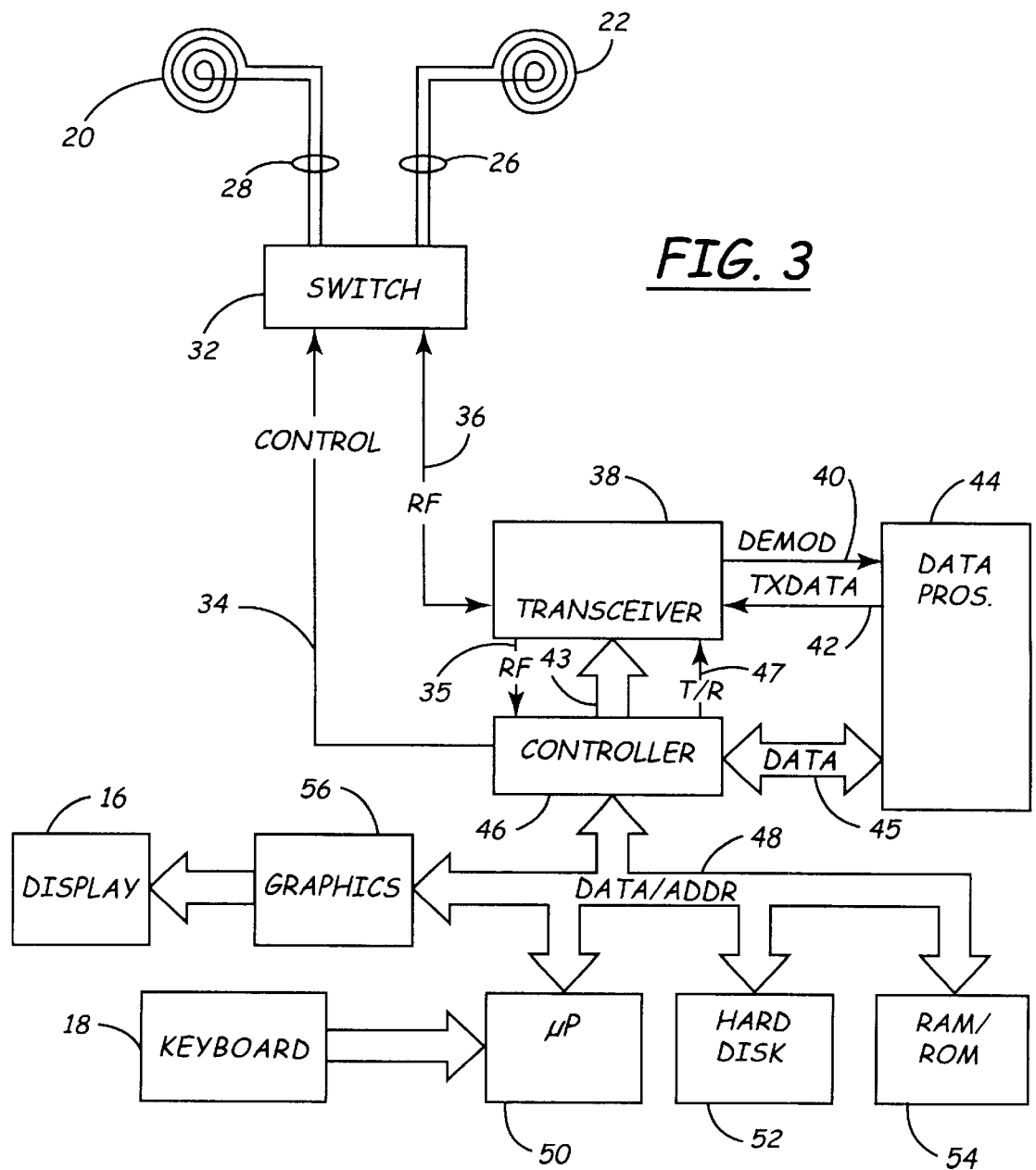
FIG. 3 is a functional diagram illustrating the interconnection of the antenna array, RF circuitry and other functional components of the programmer or monitor illustrated in FIG. 1.

FIG. 3 is a diagram illustrating the interconnection of the antenna array of the programmer or monitor 10 of FIG. 1 with the circuitry and other functional components included therein. The controller circuitry 46 selects which of the two antennas 20 and 22 is employed by means of control line 34 which controls antenna switch 32. RF signals are carried between the antenna switch 32 and transceiver 38 via RF line 36.

The circuitry within the programmer or monitor includes a microprocessor 50 which controls the operation of the device as a function of programming stored in RAM/ROM 54 and/or hard disk drive 52, both of which are coupled to the microprocessor via data/address bus 48. Commands from the physician are provided to the microprocessor via keyboard 18 and/or any additional control buttons on the telemetry head 12 (FIG. 1) and/or, if the display 16 is touch sensitive, from the display as well. Information regarding the operation of the programmer or monitor and information received from the associated implanted device are displayed on display 16, under control of graphics circuitry 56. The graphics circuitry, microprocessor, hard disk drive, RAM/ROM circuitry, keyboard and display may all correspond to corresponding components of personal computers and/or prior art programmers and monitors such as those described in the patents incorporated by reference above.

Operation of the telemetry system is controlled by controller circuit 46 which operates under control of microprocessor 50. Transceiver 38 may be any of any appropriate type, including those described in the patents referred to above. In the particular embodiment illustrated, transceiver 38 may be configurable to operate at multiple frequencies or using multiple communication protocols, under control of controller 46 via control bus 43. Controller 46 also configures the transceiver 38 to either transmit RF signals to the antennas or receive RF signals from the antennas by means of transmit/receive line 47. Controller 46 provides the data to be telemetered to the implanted device to data processing circuitry 44 and receives decoded received data from the implanted device from data processing circuit 44, via data bus 45. Data provided by controller 46 to data processing circuitry 44 is converted therein from parallel to serial format and provided serially to transceiver 38 on TX data line 42. Correspondingly, data received by transceiver 38 is provided in serial format on DEMOD line 40 to data processing circuitry 44, and is converted therein to parallel format and provided to the microprocessor 50 via controller circuitry 46. Controller 46 is also capable of monitoring the integrity of the telemetry link to allow for selection between the two antennas as described above.

In operation, during initialization of telemetry or monitoring functions requiring a telemetry link between the programmer/monitor 10 (FIG. 1) and an implanted device, the controller operates to first employ the larger diameter, outer coil antenna 20, selected by means of switch 32 under control of control line 34. In response to receipt of a valid telemetry transmission, the implanted device will in turn provide a return transmission so indicating. In the event that the received return telemetry transmission from the implanted device is acceptable, the outer coil antenna 20 is thereafter employed for purposes of maintaining the telemetry link. In the event that either no return telemetry transmission is detected using coil 20, or in the event that the return transmission is of substandard amplitude and/or has a higher error rate than acceptable, the controller may thereafter switch to inner antenna 22 for use in attempting to establish a telemetry link with the implanted device. In the event that the received return telemetry transmission from the implanted device is acceptable, the inner coil antenna 22 may thereafter be employed for purposes of maintaining the telemetry link. In the event that neither of the two coil antennas provides an acceptable telemetry link, the device may be provided with an indicator, for example in the form of an LED located on the housing of the telemetry head, or an indicator on the display 16 in the programmer or monitor 10. In such case, the physician would have to move the telemetry head 12 to reestablish a telemetry link. Similarly, in the event that after selection of the inner or outer coil antenna (22, 20), the telemetry link is thereafter lost, the controller 46 may thereafter attempt to employ one of the two antennas not previously in use to reestablish the telemetry link, and, if unsuccessful, the device may provide an indication of an inability to establish an accurate telemetry link, similarly requiring the physician to reposition the telemetry head.

The particular mechanisms employed by the controller to determine the integrity of the telemetry link may correspond to those generally known in the prior art, and may include, for example, monitoring the signal strength of the return transmission from the implanted device, as described in U.S. Pat. No. 5,683,432 issued to Goedeke et al., incorporated herein by reference in its entirety. Alternatively, the mechanism by which the programmer or monitor 10 determines the integrity of the transmission may involve a measurement of the number of errors per received transmission, as described in U.S. Pat. No. 4,531,523 issued to Anderson, also incorporated herein by reference in its entirety. However, other mechanisms for monitoring the integrity of the telemetry length may be substituted, within the confines of the present invention.

In conjunction with the physical structure of a programmer or monitor embodying the present invention, it is expected that in most cases, the outer and inner coils 20 and 22, along with mutually insulated conductors 26 and 28 will be located in the cable 13 (FIG. 1) that connects the telemetry head to the programmer or monitor 10. However, in alternative embodiments, the switching circuitry 32 illustrated in FIG. 3 might also be located in the telemetry head (FIG. 1), with control and R-F lines 34 and 36, respectively, located within the cable 13 (FIG. 1). In other embodiments, the entire programmer/monitor structure illustrated in FIG. 3 might be incorporated into a small, hand held device, for use directly applied to the patient's body. The specific physical compartmentalization of the components of the monitor or programmer 10 (FIG. 1) is not critical to successful implementation of the present invention.

Figure 4:
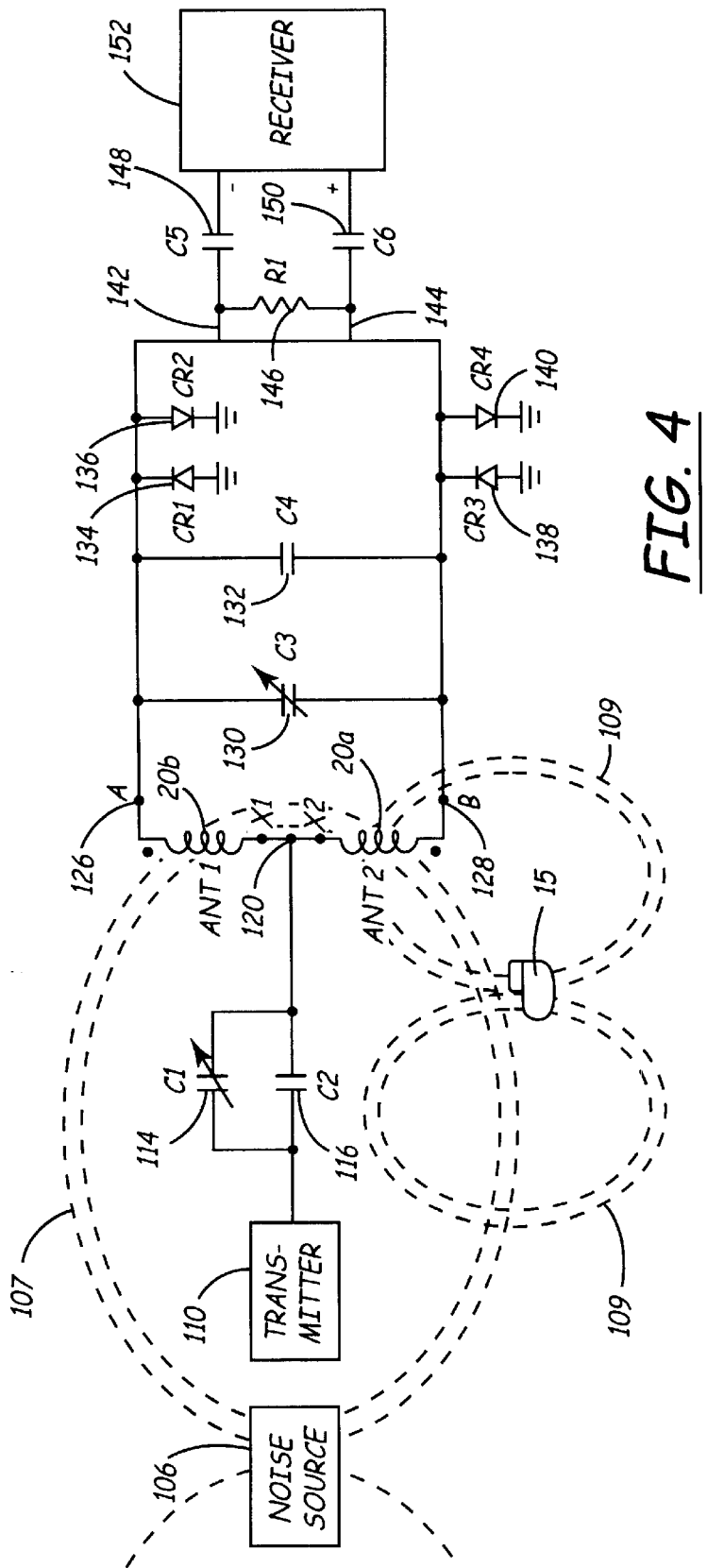
FIG. 4 is a schematic diagram of an alternative dual-coil embodiment of an antenna that may be used in the system of the present invention.

FIG. 4 is a schematic diagram of an alternative embodiment of a coil antenna that may be used in the system of the present invention. This antenna is the type shown and described in U.S. Pat. No. 4,542,532 to McQuilkin, incorporated herein by reference in its entirety. This antenna utilizes two substantially identical coils connected in series opposition to cancel noise signals common to both coils and to receive desired signals present at only one coil.

The embodiment of the dual coil antenna shown in FIG. 4 includes transmitter 110 and receiver 152, both of which would be included with the accompanying circuit components in transceiver 38 of FIG. 3. Transmitter 110 has its output connected to a parallel combination of a fixed resonant capacitor 116 and an adjustable resonant capacitor 114, which is used for resonating the antenna at the transmitter frequency. The series-resonant capacitors are connected between the transmitter circuitry and the junction point 120. Junction point 120 lies between the two series-connected antenna coils shown as 20a and 20b, which in the present embodiment, may be substituted for the single coil 20 of FIG. 3.

The two small black dots adjacent the junction points 126 and 128 of FIG. 4 indicate the polarity of winding of the coils 20a and 20b. The winding polarity is such that the coils are in series-opposition. Capacitors 130 and 132 are used to form a parallel resonant circuit with series-opposed coils 20a and 20b. Capacitor 130 provides fine-tuning of this resonant frequency.

Four diodes are employed in the transceiver circuit, two of which are electrically coupled to the electrical junction point 126 and the other two of which are coupled to the junction point 128. Diode 134 has its cathode coupled to the junction point 126 and its anode coupled to ground while diode 136 has its anode coupled to the junction point 126 and its cathode coupled to ground. Similarly, diode 138 has its cathode connected to the junction point 128 and its anode connected to ground, while diode 140 has its anode connected to junction point 128 and its cathode connected to ground. Thus, any signals that are developed across the diode pair 134, 136 or the diode pair 138, 140 will be limited in magnitude to the voltage drops that may be developed across these diodes.

The cathode of the diode 134 and the anode of the diode 136 are connected by the line 142 to one end of an antenna load resistor 146. The diodes 134 and 136 may thus be said to be "oppositely-poled." The other end of the antenna load resistor 146 is connected by the line 144 to the cathode of the diode 138 and the anode of the diode 140. The voltage developed across the load resistor 146 is coupled to the receiver 152 by the coupling capacitors 148 and 150. The field 109 from the implanted medical device 15 will have a stronger effect on coil 20a than on coil 20b. When the device is in the receive mode the signal seen at the receiver input is the difference between the voltages generated across each individual coil. The receiver 152 desirably employs a differential amplifier input stage to avoid any noise introduction due to voltage differences between the antenna and system ground.

In the receiving mode, the antenna coil 20a, which is closest to the implanted device, picks up a substantially larger signal than the more remotely located coil 20b. For example, the implanted cardiac pacemaker 15 creates a field 109 when it is transmitting telemetry information which links the coil 20a with a substantially stronger signal than the coil 20b. On the other hand, a noise source 106, positioned at a more remote location provides a field 107 which tends to link both coils, 20b and 20a, with the same field. Since the coils are wound in series opposition, however, the noise field component from the noise source 106 will be cancelled, leaving primarily the signal component at the input of the receiver 152.

During telemetry reception all of the diodes are essentially non-conductive due to the low antenna signal voltages that are typically applied across the diodes. These are generally less than 5 millivolts peak-to-peak and, therefore, diodes 134, 136 and 138, 140 effectively act as very high resistances to ground. The interference field which links the antenna coils 20b and 20a will generate equal but opposite antenna voltages which will cancel when summed at the receiver input and the common mode rejection of the receiver differential signal will also attenuate undesirable electric-field pick-up. The telemetry field thus generates antenna voltages unequally on the coils 20b and 20a. Thus the telemetry signals appear at the input of the receiver 152 through the coupling capacitors 148 and 150. During the receive mode of operation, the transmitter circuit 110 will be effectively connected to a null point between the oppositely wound coils 20b, 20a and will, thus, have no appreciable effect on the receiver circuit.

According to one embodiment of the current invention, each of the coil antennas 20 and 22 of FIG. 2 may be dual-coil antenna of the type shown in FIG. 4.

Figure 5:
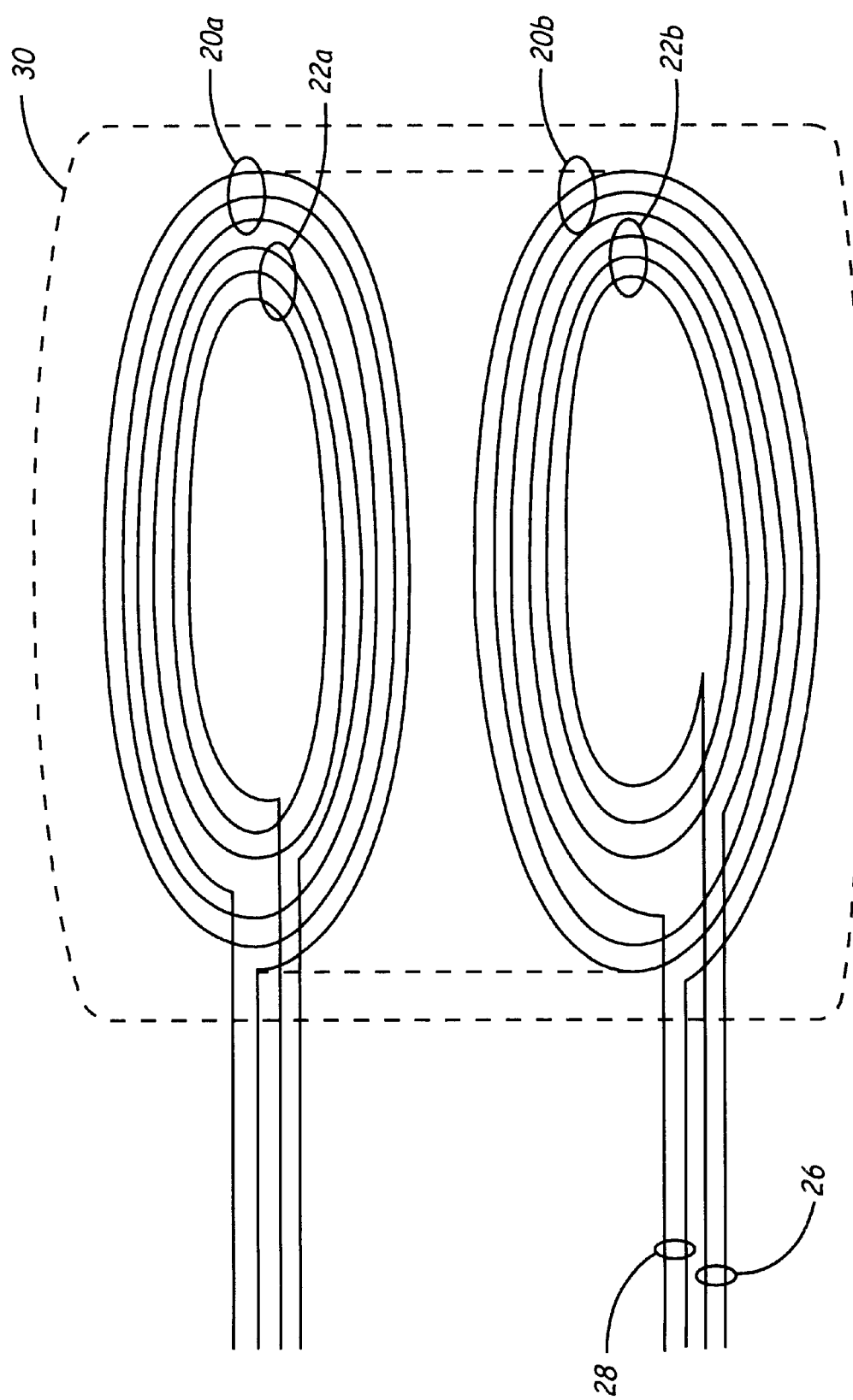
FIG. 5 is a diagram illustrating the manner in which two dual-coil antennas may be positioned with respect to each other.

FIG. 5 is a diagram illustrating the manner in which two dual-coil antennas may be positioned with respect to each other. Outer coil 20a is positioned adjacent to outer coil antenna 20b to provide improved signal-to-noise ratio as compared to the single-coil antenna 20 of FIG. 3. Similarly, inner coil 22a is positioned within outer coil 20a and adjacent to inner coil antenna 22b to provide an improved signal-to-noise ratio as compared to single-coil antenna 22. Dashed line 30 represents the enclosure housing telemetry head 12.

The embodiments of FIGS. 2 and 5 show inner and outer coil pairs that are substantially concentric, co-planar, and generally circular. It may be noted that none of these aspects are necessary for proper operation of the system. The inner coil may be of any arbitrary shape that is the same or different as compared to the arbitrary geometry of the outer coil. The inner and outer coils need not be concentric or co-planar. Furthermore, one or both of the antennas may be of the dual-coil configuration shown in FIG. 5.

Figure 6B:
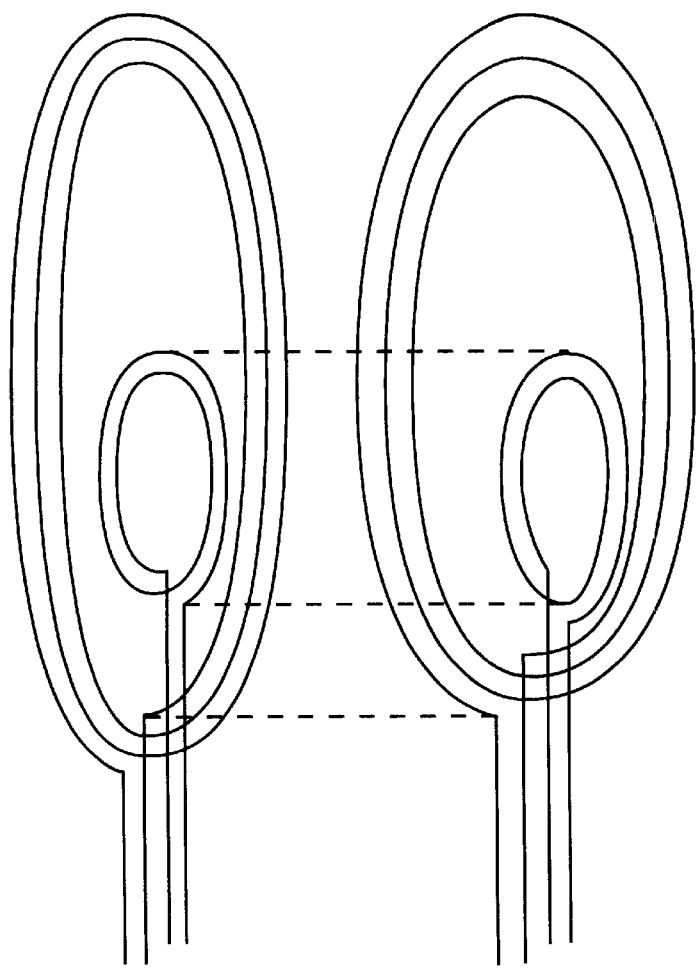
FIG. 6B is a diagram illustrating an inner and outer coil antenna wherein the inner and outer coils are not concentric, and wherein both the inner and outer coils include two coils is series opposition to improve the signal-to-noise ratio.
Figure 6A:
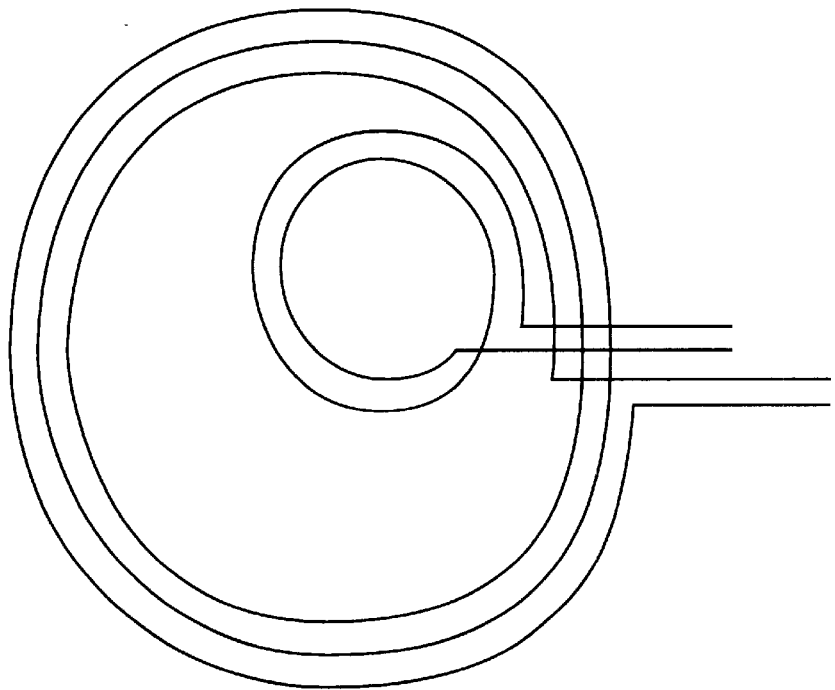
FIG. 6A is a diagram illustrating an inner and outer coil configuration wherein the inner and outer coils are not concentric.

FIG. 6A is a diagram illustrating an inner and outer coil configuration wherein the inner and outer coils are not concentric. The inner coil may be positioned anywhere within the outer coil. It may be noted that if both the inner and outer coil are dual-coil antennas of the type shown in FIG. 5, both of the inner coils must be positioned in substantially the same location with respect to the respective outer coil, and must be of substantially the same shape as discussed further below.

FIG. 6B is a diagram illustrating an inner and outer coil antenna wherein the inner and outer coils are not concentric, and wherein both the inner and outer coils are of the dual-coil configuration.

FIG. 7 is a diagram illustrating an inner and outer coil antenna wherein the inner and outer coils are not concentric or co-planar. If desired, one of the inner coils may be co-planar with respect to the associated outer coil, whereas the other inner coil may be positioned such that it is not co-planar with the respective outer coil. It may be noted that only one pair of inner and outer coils as shown in FIG. 7 is necessary to practice the current invention.

Figure 8:
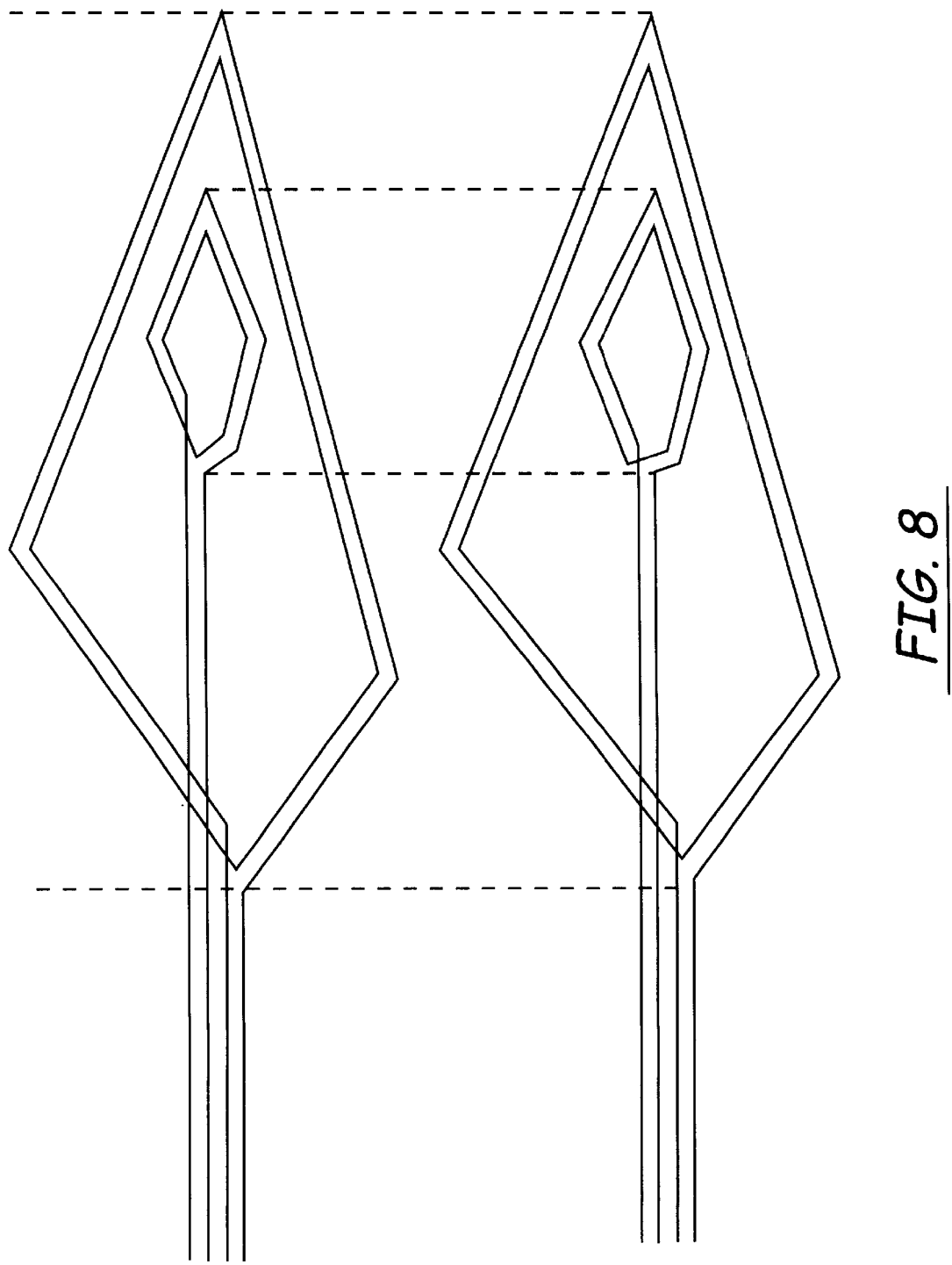
FIG. 8 is a diagram illustrating an inner and outer coil antenna wherein the inner and outer coils have arbitrary geometries with respect to each other.

FIG. 8 is a diagram illustrating an inner and outer coil antenna wherein the inner and outer coils have arbitrary geometries with respect to each other. As discussed above in reference to FIG. 7, although the geometry of an inner coil need not be the same as that of the outer coil, the geometry and spatial relationship of the two inner coils with respect to each other must be substantially similar. The same is true of the geometry and spatial relationship of the two outer coils with respect to each other. As discussed above in reference to FIG. 7, only one pair of inner and outer coils is necessary to practice the current invention. Additionally, if desired, each of the inner coils need not be in the same plane as the respective outer coil.

Figure 9:
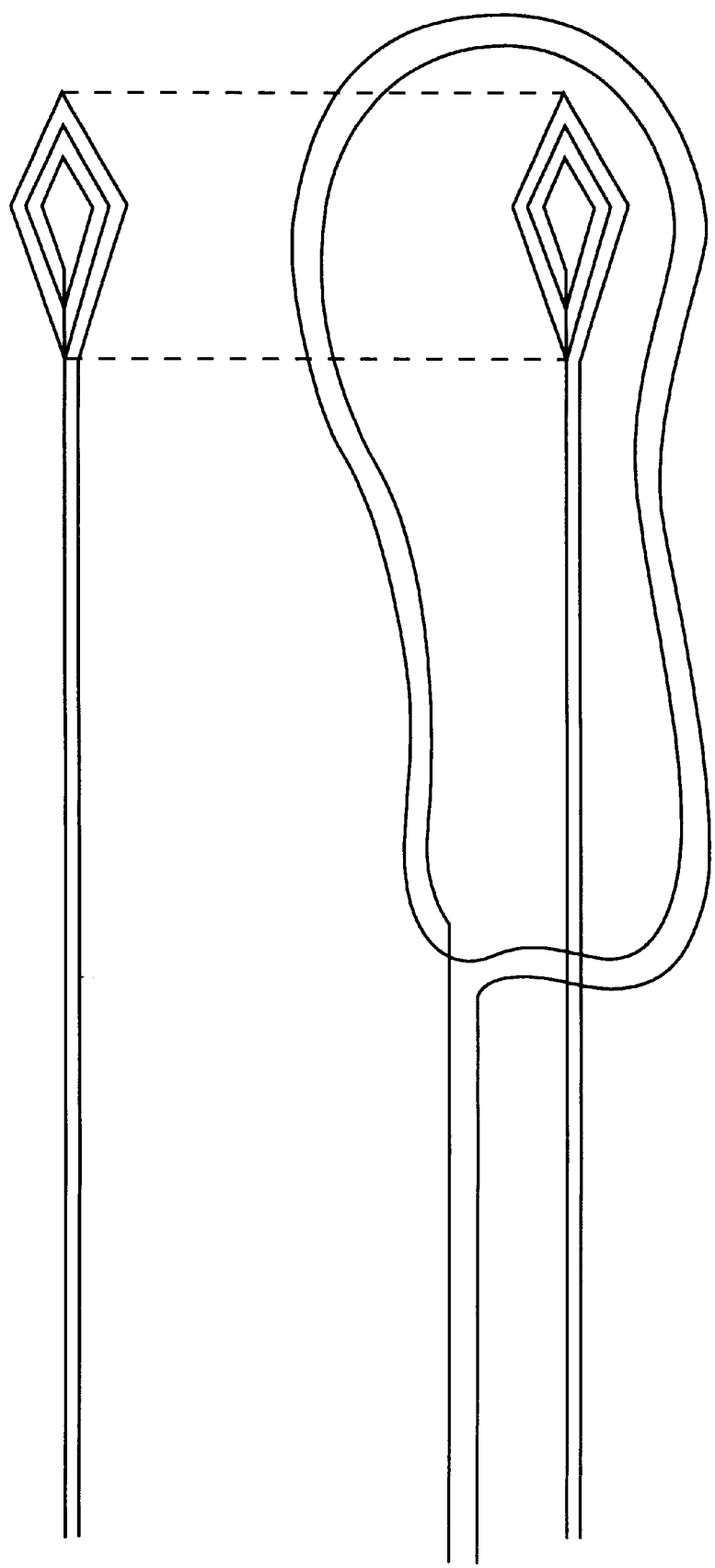
FIG. 9 is a diagram illustrating an inner and outer coil antenna wherein only the inner coil is of a dual-coil configuration.

FIG. 9 is a diagram illustrating an inner and outer coil antenna wherein only the inner coil is of a dual-coil configuration. The second inner coil is not necessary to practicing the current invention. If desired, a second outer coil may be added.

Figure 10:
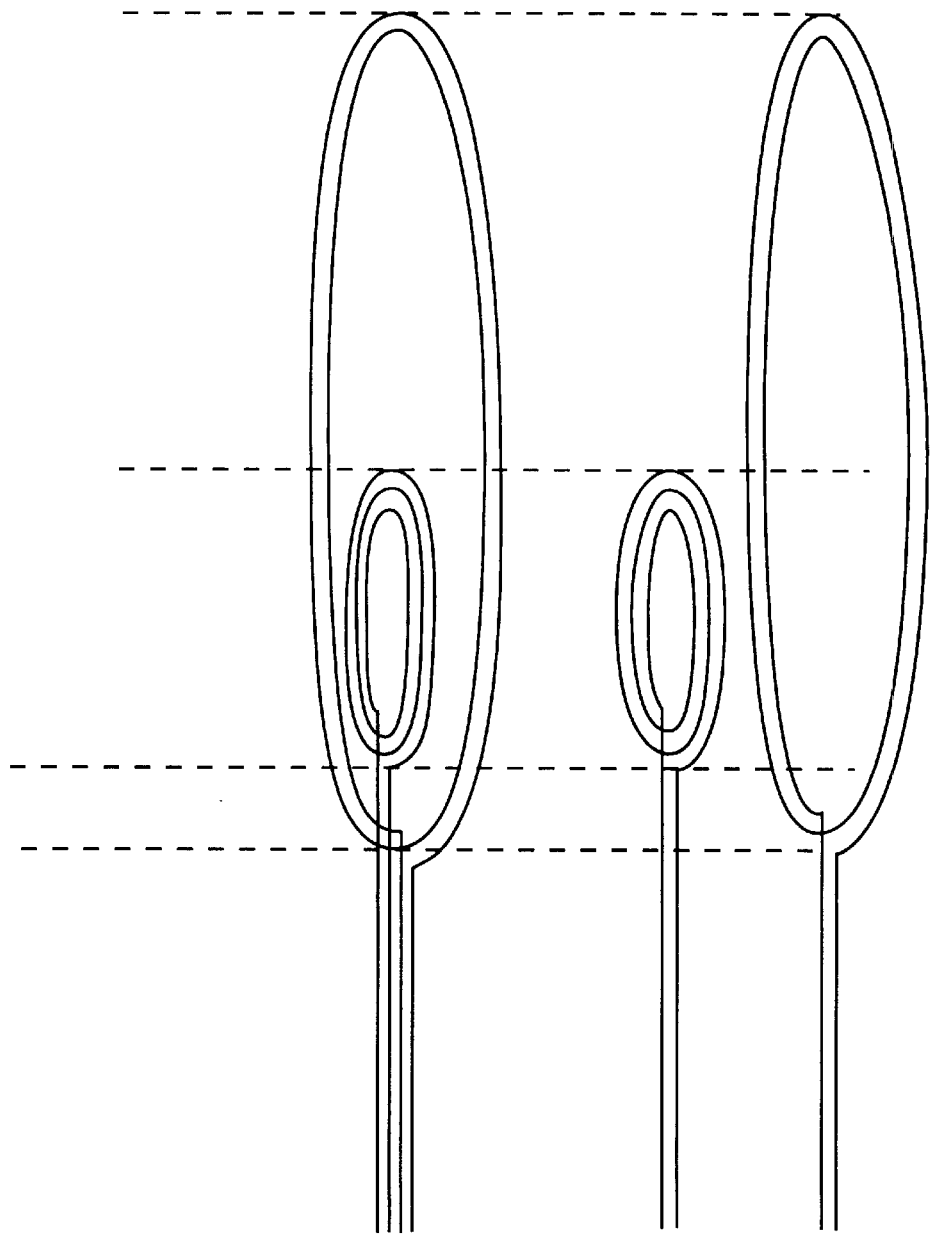

FIG. 10 is a diagram illustrating an inner and outer coil antenna wherein one of the inner coils is co-planar with respect to an associated outer coil, and wherein the other inner coil is not co-planar with respect to the associated outer coil.

The embodiments of FIGS. 6A through 10 illustrate that the spatial relationship, and the geometry, of the inner coil with respect to an associated outer coil, may vary. However, if a two-coil inner antenna is used, these two inner coils must be of substantially the same size and geometry, and include the same number of turns with respect to each other. These inner coils must further be positioned in substantially the same location with respect to the associated outer coil. That is, the inner coils are vertically "stacked" with respect to each other. Similarly, when a two-coil outer antenna is used, the two outer coils must be of substantially the same size and geometry, and include the same number of turns. These two outer coils are also vertically stacked with respect to each other.

In conjunction with the above specification, I claim:

1. An apparatus for communicating with a device implanted within a patient's body, comprising:
   a telemetry head comprising a major surface adapted to be placed adjacent the patient's body and comprising first and second coil antennas located generally parallel to the major surface;
   a transceiver;
   a switching circuit for selectably coupling the transceiver to either of the first or second antennas; and
   means for determining integrity of communications between the transceiver and an implanted device and wherein the switching circuitry selectably couples the transceiver to the first or second antenna as a function of the integrity of the communications.

2. The apparatus according to claim 1, wherein at least one of the first and second coil antennas includes first and second coils coupled in series opposition to one another to provide improved signal-to-noise ratio.

3. The apparatus according to claim 2, wherein both of the first and second coil antennas includes first and second coils coupled in series opposition to one another, wherein the first coil of the first coil antenna is co-planar with respect to the first coil of the second coil antenna, and wherein the second coil of the first coil antenna is co-planar with respect to the second coil of the second coil antenna.

4. The apparatus according to claim 1, wherein the telemetry head further comprises a permanent magnet to activate a reed switch within the device implanted within the patient's body.

5. The apparatus according to claim 1, and further including a control circuit coupled to the switching circuit to control the selectable coupling by the switching circuit of the transceiver to the first or second antennas.

6. The apparatus according to claim 5, further including a storage device to store programmed data signals; and a microprocessor coupled to the control circuit and the storage device, the microprocessor operating under the control of the programmed data signals to control the operations of the control circuit.

7. The apparatus according to claim 1, wherein the first and second coil antennas are concentric with respect to each other.

8. The apparatus according to claim 1, wherein the first and second coil antennas are co-planar with respect to each other.

9. The apparatus according to claim 1, wherein the first coil antenna has a different geometry with respect to the second coil antenna.

10. A method of communicating with a device implanted within a patient's body, comprising:

placing adjacent the patient's body a major surface of a telemetry head comprising first and second coil antennas located generally parallel to the major surface;

employing a transceiver to communicate with the implanted device;

employing a switching circuit to selectably couple the transceiver to either of the first and second antennas; and determining integrity of communications between the transceiver and an implanted device and employing the switching circuitry to selectably couple the transceiver to the first or second antenna as a function of the integrity of the communications.

11. The method according to claim 10, further comprising providing, for at least one of the first and second coil antennas, first and second coils coupled in series opposition to one another to provide improved signal-to-noise ratio.

12. The method according to claim 10, further comprising employing a permanent magnet to activate a reed switch within the device implanted within the patient's body.

13. The method according to claim 10, further comprising controlling the selectable coupling by the switching circuit of the transceiver to the first or second antennas utilizing a control circuit.

14. The method according to claim 13, further comprising:

storing programmed data signals in a storage device; and controlling the operations of the control circuit via a microprocessor executing under the control of the programmed data signals.

15. The method according to claim 10, wherein the first and second coil antennas are in different planes with respect to one another.

16. The method according to claim 10, wherein the first and second coil antennas are not concentric with respect to each other.

* * * * *